US008175833B2

(12) United States Patent
White

(10) Patent No.: US 8,175,833 B2
(45) Date of Patent: May 8, 2012

(54) SYSTEM AND METHOD FOR MULTI-AXIS SIMULATION

(75) Inventor: Andrew D. White, Minneapolis, MN (US)

(73) Assignee: Bose Corporation, Framingham, MA (US)

( * ) Notice: Subject to any disclaimer, the term of this patent is extended or adjusted under 35 U.S.C. 154(b) by 689 days.

(21) Appl. No.: 12/145,822

(22) Filed: Jun. 25, 2008

(65) Prior Publication Data

US 2009/0326837 A1 Dec. 31, 2009

(51) Int. Cl.
*G01D 18/00* (2006.01)
*G06G 7/48* (2006.01)

(52) U.S. Cl. ............................................ 702/88; 703/7

(58) Field of Classification Search .................... 702/88, 702/33–36, 41–44, 81, 84, 108, 113, 123, 702/127, 138–139, 150–154, 182–183, 189; 703/1, 6–7; 73/760, 787–788, 798, 805–806, 73/811–812, 816, 819, 849, 852, 854, 856–857, 73/859, 862.041–862.045
See application file for complete search history.

(56) References Cited

U.S. PATENT DOCUMENTS

| 4,802,365 A | 2/1989 | Sallberg et al. | |
| 7,546,775 B2* | 6/2009 | Chinavare | 73/849 |
| 7,624,648 B2* | 12/2009 | Nickel et al. | 73/856 |
| 2002/0162400 A1 | 11/2002 | Xie et al. | |

FOREIGN PATENT DOCUMENTS

| WO | 2009003081 A2 | 12/2008 |
| WO | 2009157966 A1 | 12/2009 |

OTHER PUBLICATIONS

Soderling et al., Servo Controller Compensation Methods Selection of the Correct Technique for Test Applications, 1999, Society of Automotive Engineerings, Inc., 14 pp.*
International Search Report and Written Opinion dated Mar. 24, 2010 for Int. Appl. No. PCT/US2009/044604.
Dougherty JJ et al: "Modeling and Identification of a Triaxial Shaker Control System", Control Applications, 1995., Proceedings of the 4th IEEE Conference on Albany, NY, USA Sep. 28-29, 1995, NY, NY, USA. pp. 884-889.
Joan E Sanders et al: "A Bidirectional Load Applicator for the Investigation of Skin Response to Mechanical Stress", IEEE Transactions on Biomedicalengineering, IEEE Service Center, Piscataway, NJ, US, vol. 44, No. 4, Apr. 1, 1997.
Written Opinion of the International Preliminary Examining Authority dated Aug. 17, 2010 for PCT/US2009/044604, 5 pages.
International Preliminary Report on Patentability dated Sep. 15, 2010 for PCT/US2009/044604, pp. 10.

* cited by examiner

*Primary Examiner* — Toan M Le
(74) *Attorney, Agent, or Firm* — Bose Corporation

(57) ABSTRACT

A multi-axis fatigue testing device includes a multiple input, multiple output mechanical linkage driven by a plurality of actuators and a controller operating each of the plurality of actuators in real time and in synchronization to produce user-defined multiple fatigue cycle profiles. A startup method enables a sample mounted at an arbitrary multi-axis state to receive a desired simulation profile while maintaining the sample below any of the extremum values of the desired simulation profile.

14 Claims, 8 Drawing Sheets

SYSTEM AND METHOD FOR MULTI-AXIS SIMULATION

BACKGROUND

This disclosure relates to testing devices and methods for medical implant devices.

SUMMARY

A multi-axis fatigue testing device includes a multiple input, multiple output mechanical linkage driven by a plurality of actuators and a controller operating each of the plurality of actuators in real time and in synchronization to produce user-defined multiple fatigue cycle profiles. A startup method enables a sample mounted at an arbitrary multi-axis state to receive a desired simulation profile while maintaining the sample below any of the extremum values of the desired simulation profile.

One embodiment of the present invention is directed to a startup method for a multi-axis simulation system comprising: providing a test fixture having a MIMO linkage, the MIMO linkage driven by a first actuator and a second actuator, the MIMO linkage acting on a sample to provide simulation along a first simulation axis and a second simulation axis; calculating an initial position for the first actuator; moving the first actuator to the initial position; operating the first actuator according to a first simulation axis profile, the first simulation axis profile characterized by a first profile amplitude, and a second simulation axis profile, the second simulation axis profile characterized by a second profile amplitude; and increasing the first profile amplitude from an initial value of zero to a desired first profile amplitude at a predetermined rate. In an aspect, the predetermined rate is less than 9% per cycle. In an aspect, the predetermined rate is 1% per cycle. In an aspect, the first simulation axis is an axial strain. In an aspect, the second simulation axis is a bend angle. In an aspect, the initial position is calculated from a point in a region containing a middle half of a peak-to-peak range of the first simulation axis and a middle half of a peak-to-peak range of the second simulation axis. In an aspect, the initial position is calculated from a mean value of the first simulation axis profile and a mean value of the second simulation axis profile. In an aspect, the initial position is calculated from one-half of a value of the first simulation axis. In an aspect, the method includes operating the first actuator to disengage a bend tool contacting the sample; operating the second actuator to an initial position calculated for the second actuator; and operating the first actuator to the initial position calculated for the first actuator. In one aspect the method may be stored as computer-executable instructions on a computer-readable medium.

Another embodiment of the present invention is directed to a multi-axis simulation system comprising: a test fixture having a MIMO linkage, the MIMO linkage driven by a first actuator and a second actuator, the MIMO linkage acting on a sample to provide simulation along a first simulation axis and a second simulation axis; a controller configured to operate the first and second actuators according to a user-specified first simulation profile and a second-simulation profile, the controller further configured to start operation of the MIMO linkage to track the first and second simulation profile and constrain first simulation axis values applied to the sample to within a peak-to-peak range characterizing the first simulation profile. In an aspect, the first simulation axis is an axial strain and the second simulation axis is a bend angle. In an aspect, a first torsion assembly is connected to a first end of the sample and a second torsion assembly is connected to a second end of the sample, the first and second torsion assemblies driven by a third actuator according to a user-specified third simulation profile. In a further aspect, the third actuator is operated simultaneously by the controller independently of the first and second actuators. In an aspect, the system further comprises a flow path providing a fluid flow through the sample according to a user-specified fourth simulation profile. In a further aspect, the system comprises a pump providing a pulsatile flow in the flow path.

Another embodiment of the present invention is directed to a computer-readable medium comprising instructions for controlling a computer to execute a startup procedure on a multi-axis simulation system by: calculating an initial position for a scissors actuator; moving the scissors actuator to the initial position; operating the scissors actuator and an extensor actuator, the scissors and extensor actuators driving a test fixture having a MIMO linkage, the MIMO linkage acting on a sample to provide simulation according to a first simulation profile along a first simulation axis and according to a second simulation profile along a second simulation axis; and increasing an amplitude having an initial value of zero to a value characterizing an amplitude of the first simulation profile at a predetermined rate. In an aspect the computer-readable medium includes instructions for controlling the computer to operate a torsion actuator driving a mechanical linkage causing a first torsion assembly connected to a first end of a sample holder supporting the sample and a second torsion assembly connected to a second end of the sample holder to apply a torsion to the sample according to a user-specified torsion simulation profile. In an aspect, the torsion actuator is operated in parallel with the first and second actuators to apply the first, second, and torsion simulation profiles to the sample simultaneously. In an aspect the computer-readable medium includes instructions for controlling the computer to: operate the extensor actuator to disengage a bend tool contacting the sample; operate the scissors actuator to an initial position calculated for the scissors actuator; and operate the extensor actuator to the initial position calculated for the extensor actuator.

DETAILED DESCRIPTION

Figure 1:
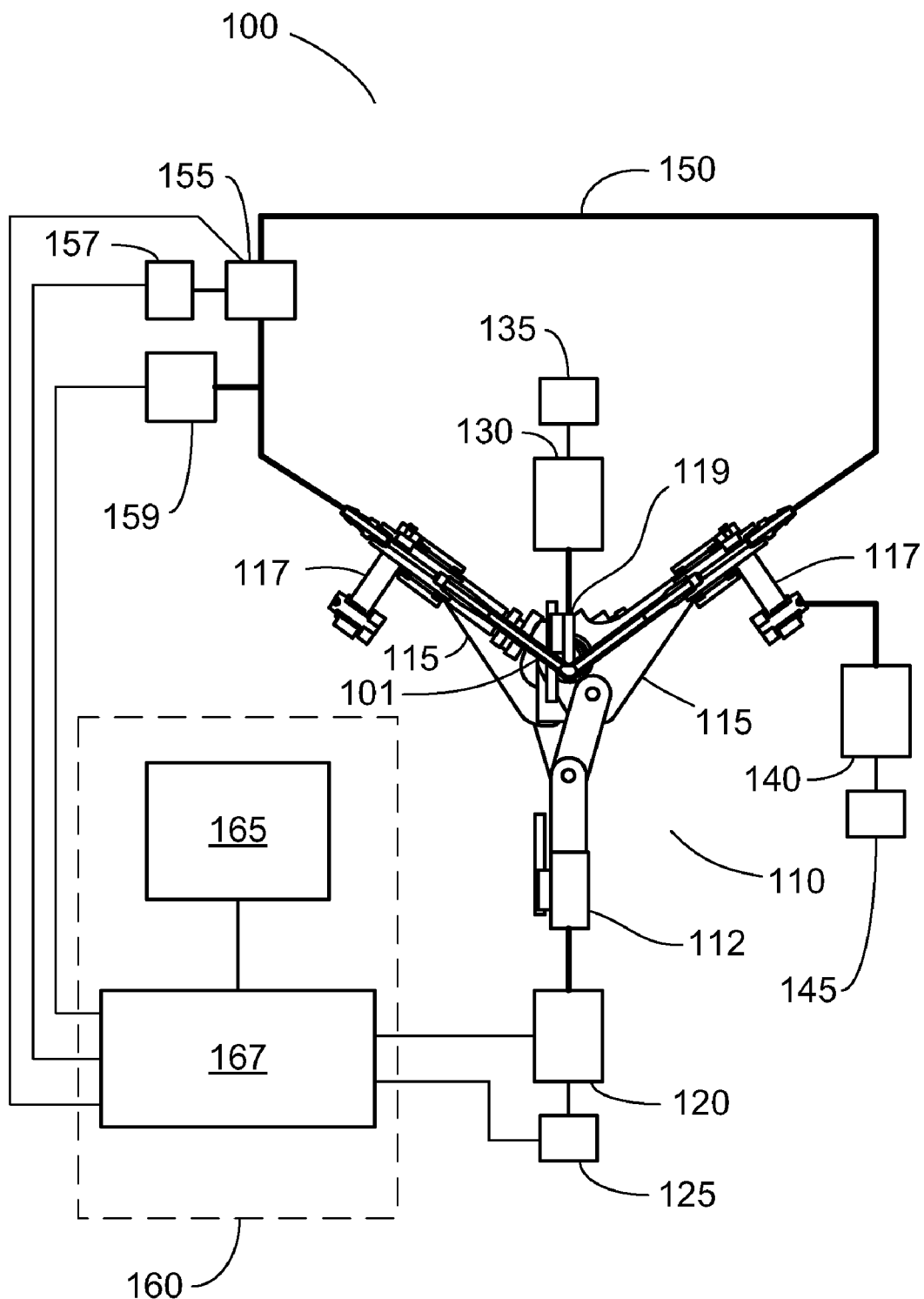
FIG. 1 is a schematic diagram illustrating an embodiment of a multi-axis simulation system.

FIG. 1 is a schematic diagram illustrating an example of a multi-axis simulation system 100. In FIG. 1, a sample is held in a sample holder 101 that is attached to a multi-axis test fixture 110. The sample is preferably an implantable stent but other implantable devices or bioprosthesis devices may be tested with the simulation system 100 shown in FIG. 1.

Test fixture 110 includes a pair of lever arms 115 that are rotatable around a common pivot point. Each lever arm 115 is mechanically linked to a common drive link 112 that is connected to a drive shaft of a first actuator 120, herein referred to as a scissors actuator. As the common drive link 112 is displaced upward in FIG. 1, the lever arms 115 rotate downward around the common pivot point thereby increasing a bend angle of the sample holder 101. As the common drive link 112 is displaced downward in FIG. 1, the lever arms 115 rotate upward toward each other and decreases the bend angle of the sample holder 101. The bend angle of the sample holder is the angle formed by the sample holder ends and a contact point where a bend tool 119 contacts the sample holder 101.

The bend tool 119 contacts the sample holder 101 about midway along the length of the sample holder 101. As the bend tool 119 is displaced downward in FIG. 1, the bend tool 119 axially strains the sample while also bending the sample held in the sample holder 101. The bend tool 119 is driven by a second actuator 130, herein referred to as an extensor actuator. The bend tool may have a curved surface that contacts the sample holder. Other examples of bend tools that may be used are described in U.S. application Ser. No. 11/757,772 filed Jun. 4, 2007, herein incorporated by reference in its entirety.

Each lever arm 115 supports a torsion assembly 117. Each torsion assembly 117 supports an end of the sample holder 101 and is configured to provide a flow path 150 to the sample holder 101 and apply a rotation around a longitudinal axis of the sample holder 101. Rotation of the sample holder 101 is driven by a third actuator 140, herein referred to as a torsion actuator. In a preferred embodiment, a mechanical linkage may be coupled to the third actuator 140 and to each torsion assembly 117 such that each end of the sample holder 101 is rotated in an opposite direction when driven by the third actuator 140.

Flow path 150 directs a fluid through the sample and sample holder 101. A fourth actuator 155, herein referred to as a pump, moves the fluid around the flow path and may be monitored by a pump sensor 157. In a preferred embodiment, pump 155 provides a pulsatile flow through the flow path 150. In other embodiments, pump 155 may provide a mean flow rate through the flow path. In other embodiments, pump 155 may be operated to provide a mean pressure at the sample. It is believed that a pulsatile flow through the sample causes a hoop strain in the sample that more closely simulates an in-use condition of the sample in, for example, an artery. A flow path sensor 159 monitors one or more conditions of the fluid in the flow path. Examples of flow path sensors include, without being limiting, pressure sensors, mass or volume flow sensors, pH sensors, particle sensors, temperature sensors, and chemical sensors. The fluid may be a saline mixture that simulates the expected characteristics of a fluid contacting the sample during use. The fluid may include nutrient media that can support live cells if the sample contains living cells.

The view shown in FIG. 1 shows only one sample but the multi-axis test fixture 110 is preferably configured to support more than one sample and more preferably support at least 10 samples simultaneously. Each sample may be connected to a separate flow path or groups of samples may share a flow path.

A controller 160 manages the operation of the simulation system 100 and includes a computer 165 and an interface module 167. The computer 165 includes I/O devices such as a display for viewing information and input devices such as a keyboard, mouse, touch pad, or other similar devices for entering information into the computer. The computer 165 includes a processor that executes a control program and computer-readable medium that stores the control program and data received from a user or sensors 125, 135, 145, 157, 159. Interface module 167 receives commands from the computer and operates each of the actuators 120, 130, 140, 155 in response to the received commands and to data from sensors 125, 135, 145, 157, 159. For the purposes of clarity, FIG. 1 does not show all the control lines between the interface module 167 and each sensor and actuator.

The control program enables a user to select or set various parameters that define the operation of the multi-axis simulator. An example of such a control program is the WinTest® Controls program available from the ElectroForce Systems Group of Bose Corporation of Eden Prairie, Minn. For example and without being limiting, if a user wants to perform a fatigue test on the sample, the user may enter the number of fatigue cycles to perform and cycle profiles for each of the desired simulation axes, referred to herein as simulation profiles. Each cycle profile may be designed independently of the other cycle profiles. For example, the user may select a heartbeat-style wave profile from a list of predetermined cycle profiles for the pulsatile pump and enter the desired cycle frequency and the maximum and minimum values for the desired pump pressure. Without being limiting other examples of predetermined cycle profiles may include a sinusoidal profile, a square profile, a triangular profile, and profiles simulating conditions at various points of a human body. The user may select a sine wave profile for the torsion applied to the sample and enter the desired torsion cycle frequency, the maximum and minimum values for the desired torsion profile, a mean torsion, and a phase angle. The user may enter a user-defined bend profile and a different user-defined axial strain profile. The control program stores the entered data and periodically sends commands to the interface module to control the operation of the test such that the sample is subjected to each of the simulation profiles simultaneously during the fatigue test. The control program receives sensor information from the interface module and stores the sensor information for later analysis.

In the configuration shown in FIG. 1, the sample experiences simultaneous simulation along four axes; hoop strain, torsion, axial strain and bend angle. It is believed that multi-axis simulation provides a more realistic simulation of expected in-use conditions and provides more reliable information relative to information from a simple bend fatigue test. The sample hoop strain is dominated by the pulsatile flow profile and can be run independently of the other simulation axes without significant coupling. Similarly, the sample torsion is dominated by the axial rotation controlled by the torsion actuator 140 following the user-input torsion profile and can also be run independently of the other simulation axes without significant error. The sample axial strain and bend angle, however, result from a combination of displacements from the scissors actuator 120 and the extensor actuator 130 due to the mechanical linkages of the test fixture 110. The linkage between the axial strain and bend angle simulation axes is sufficiently strong such that a sinusoidal profile applied to both the scissors actuator and extensor actuator can result in a non-sinusoidal sample axial strain and bend angle. Furthermore, the maximum sample axial strain or bend angle may be greater than the desired maximum when the linkage between the axial strain and bend angle simulation axes is not taken into account. The test fixture 110 shown in FIG. 1 is an example of a multiple-input-multiple-output (MIMO) linkage. In the example of FIG. 1, the multiple inputs are the displacements, also referred to as the position, of the scissors actuator and extensor actuator and the multiple outputs are the sample axial strain and sample bend angle. Although the user can specify the axial strain independently of the bend angle, the scissors actuator should not be operated independently from the extensor actuator because the movement of either of the scissors actuator or the extensor actuator can affect the axial strain and bend angle of the sample. U.S. application Ser. No. 11/768,675 filed Jun. 26, 2007 describes methods for controlling MIMO linkages and is incorporated herein by reference in its entirety.

Figure 2:
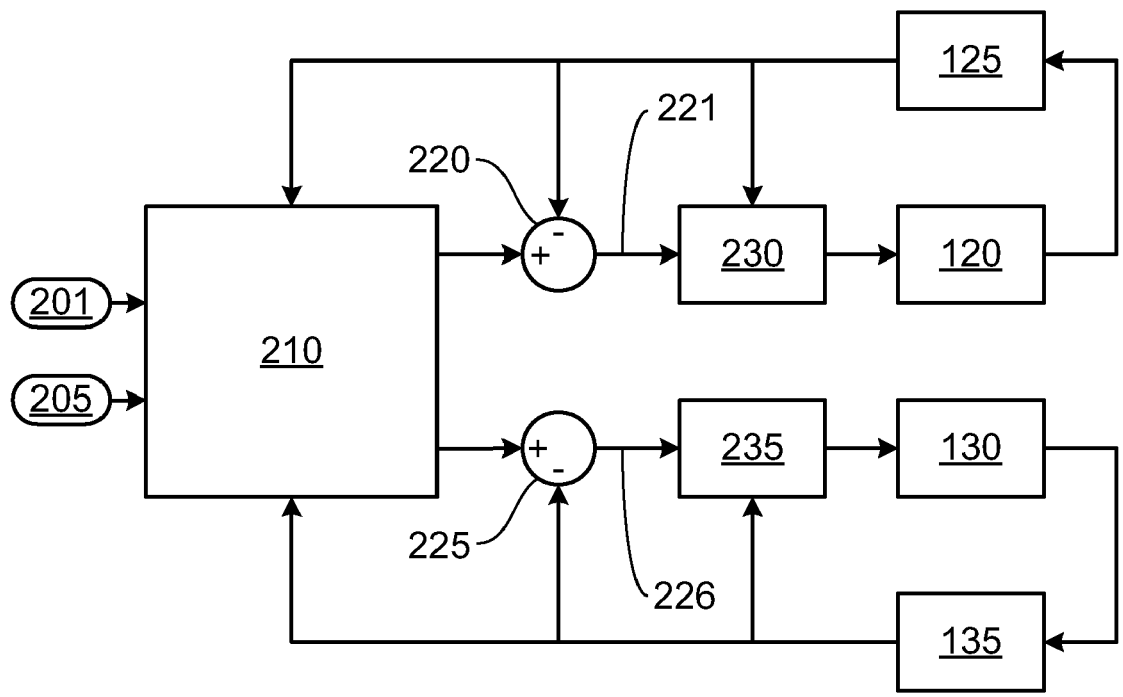
FIG. 2 is a block diagram of a portion of a controller for the system shown in FIG. 1.

FIG. 2 is a block diagram of a portion of a controller for the system shown in FIG. 1 where the same reference number refers to the same structure. In FIG. 2, user-defined cycle profiles for sample axial strain 201 and sample bend angle 205 are sent to a waveform sequence generator 210. The waveform sequence generator 210 converts the user-defined strain and bend angle values to actuator displacements based on a geometric model of the test fixture stored in the computer. Each actuator 120, 130 is controlled by a feedback controller 230, 235, respectively. Sensors 125 and 135 monitor a position of the drive shaft of actuators 120 and 130, respectively. Actuators 120 and 130 are preferably moving magnet linear motors although other embodiments may use other types of actuators to operate the test fixture. Sensors 125 and 135 are preferably LVDT position sensors although other embodiments may use other types of sensors available in the sensor art. A summing module 220, 225 generates an error signal 221, 226 representing a difference between the actuator displacement from the waveform sequence generator 210 and the sensed displacement from sensors 125, 135. Error signals 221 and 226 are input to their respective feedback controllers 230 and 235.

Prior to running a test, the user will typically mount one or more samples and sample holders on the test fixture. Mounting the sample holder will usually result in the actuator positions being in a known but arbitrary position that most likely does not correspond to a position combination in the desired cycle profile. If a test is started using the user-defined cycle profiles from an arbitrary position, the error signals 221 and 226 may be large and it may require a few cycles before the system begins tracking the desired cycle profiles. During this initial operation, the maximum values of the desired axial strain or bend angle profiles may be exceeded and lead to premature failure of the sample.

Figure 3:
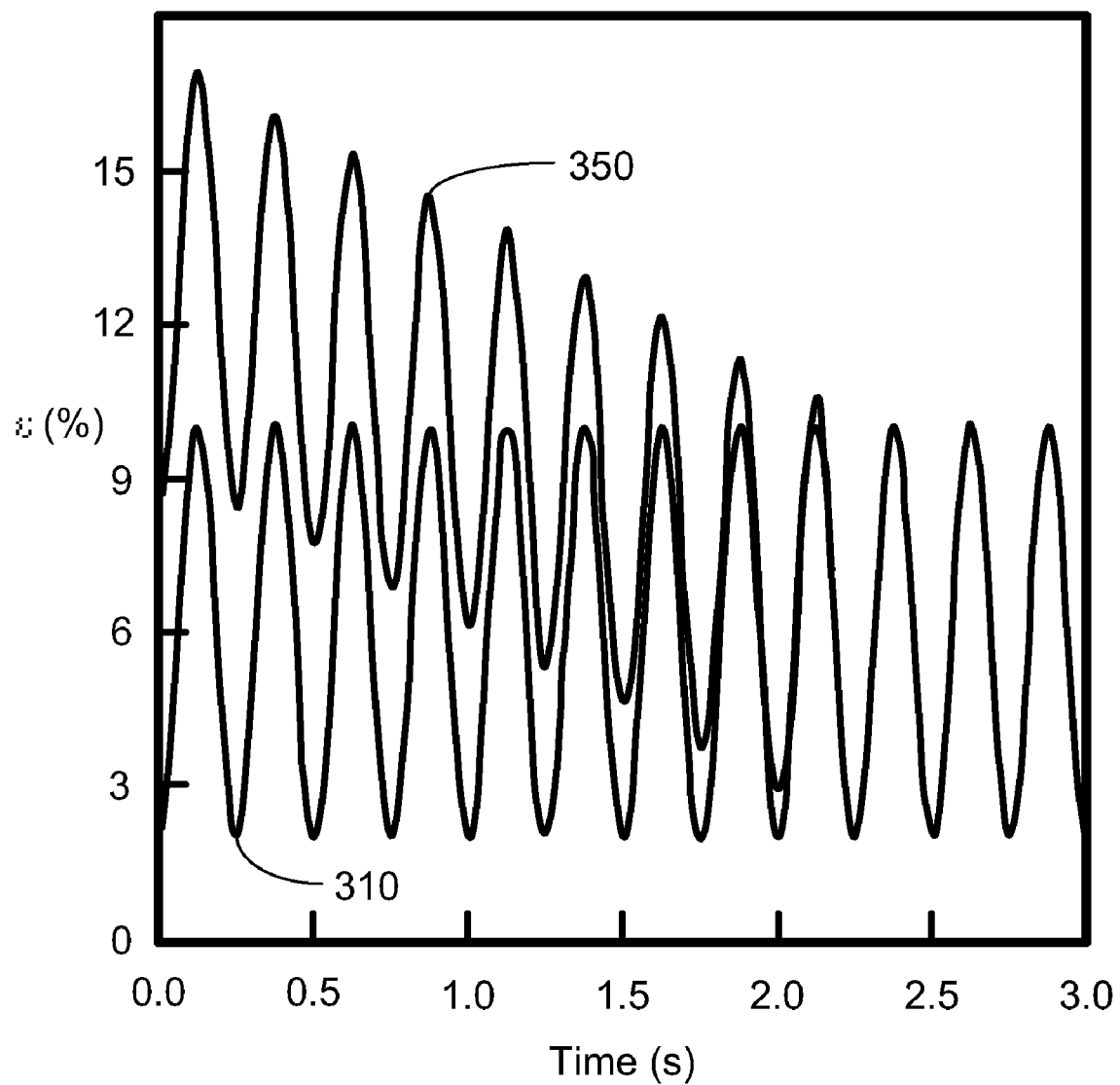
FIG. 3 is a plot illustrating a behavior of a simulation axis during a startup portion of a test.

FIG. 3 illustrates a possible behavior of the sample axial strain during startup from an arbitrary initial position. In FIG. 3, the desired axial strain cycle profile is indicated by reference 310 and shows an axial strain profile that is sinusoidal having a frequency of about 4 Hz and peak-to-peak strain values of +2% and +10%. A sample axial strain calculated from the actuator positions and following the desired axial strain profile is indicated in FIG. 3 by reference 350. The calculated sample axial strain 350 tracks the desired axial strain 310 within a few seconds but the calculated sample axial strain exceeds the desired maximum value of +10%. In the illustration shown in FIG. 2, the sample may experience a peak axial strain of about 17% during the first few seconds on the test. The large excess strain may cause premature failure or invalidate the results of the test.

Figure 4:
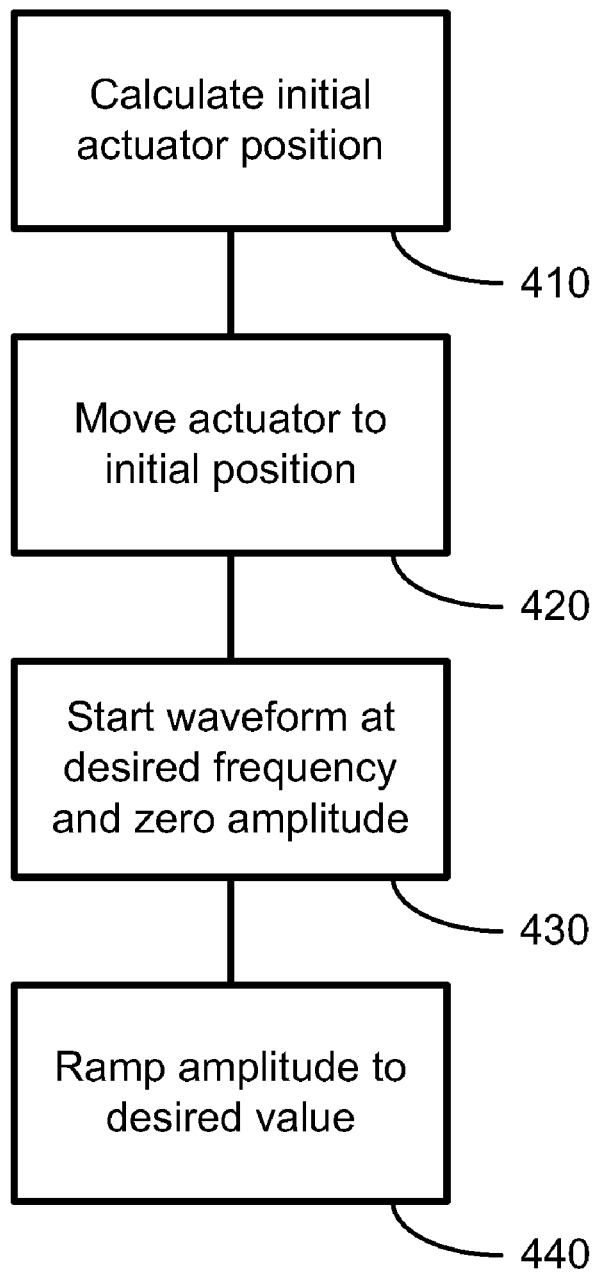
FIG. 4 is a flow diagram illustrating a startup procedure for the simulation system.

FIG. 4 is a flow diagram illustrating a startup procedure that can eliminate or at least greatly reduce the occurrence of excess sample deformation during the initial operation of a test. In step 410, initial actuator positions are calculated based on the user-defined axial strain profile and bend angle profile. For example, a desired axial strain profile may vary between 2% and 10% and a desired bend angle may vary between 10° and 55°. The actuator positions corresponding to the mean strain value of 6% and mean bend angle of 32.5° are calculated using a geometric model of the test fixture. Although a mean value is selected to initially position the actuators, a range of values may be used that avoid exceeding the extremum values of the desired profiles during the startup procedure. It is expected that a region spanning a central half of the peak-to-peak range of each simulation axis is sufficiently far from the extremum values that the sample does not exceed the extremum values during the startup procedure. Using the example above, any combination of an initial strain value between 4% and 8% (the central half of the 2-10% range of the axial strain simulation axis) and an initial bend angle between 21° and 44° (the central half of the 10-55° range of the bend angle simulation axis) may be used to calculate the initial actuator positions.

If the user enters a constant value for one of the simulation axis, one-half of the constant value is used as the mean value for that simulation axis. For example, if the user desires a fatigue test run at a constant axial strain of 12%, a value of 6% is used for the calculation of the initial actuator positions.

In step 420, actuators are moved to the initial position calculated in the previous step. The extensor actuator 130 is operated to disengage the bend tool 119 from contacting the sample holder 101. The scissors actuator 120 is then moved to the calculated initial position for the scissors actuator 120. The extensor actuator is then moved to the calculated initial position for the extensor actuator.

In step 430, the waveform is started at the desired frequency but with the amplitudes set initially to zero. In step 440, the amplitudes are increased to the desired values at a rate that is preferably less than 10% per cycle and more preferably about 1% per cycle. In a preferred embodiment, step 420 may be performed before step 430. In other embodiments, step 420 may be performed with step 430.

Figure 5:
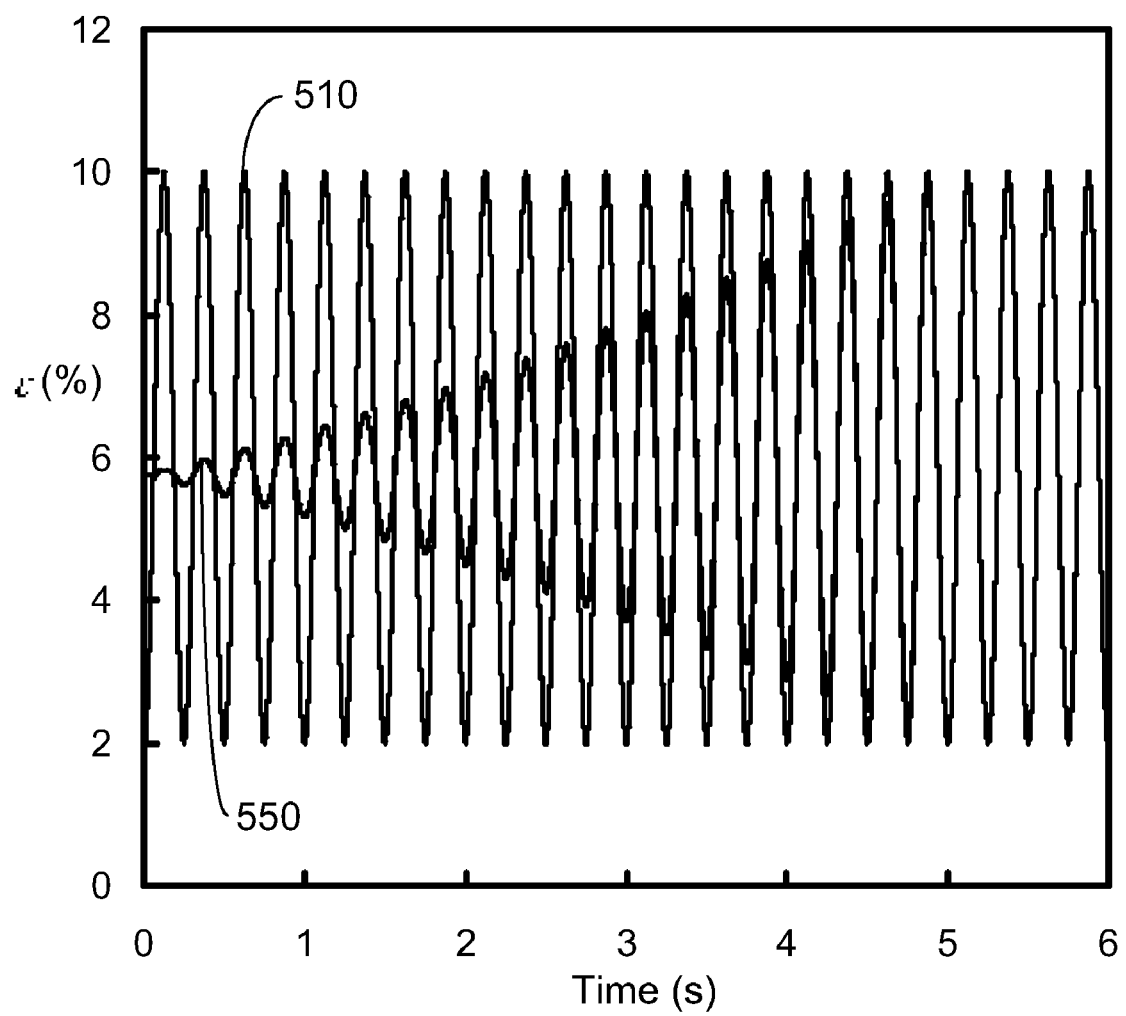
FIG. 5 is a plot illustrating a behavior of a first simulation axis during the startup procedure shown in FIG. 4.

FIG. 5 is a plot of the axial strain as a function of time using the startup procedure shown in FIG. 4. In FIG. 5, reference 510 indicates the user-desired axial strain profile and reference 550 indicates the calculated axial strain based on the drive shaft positions of the scissors actuator and the extensor actuator. In FIG. 5, the desired axial strain profile is roughly sinusoidal having a frequency of about 4 Hz and a peak-to-peak range of about +2% to +10%. The axial strain calculated from the positions of the scissors and extensor actuators shows increasing amplitude to the desired amplitude within a few seconds.

Figure 6:
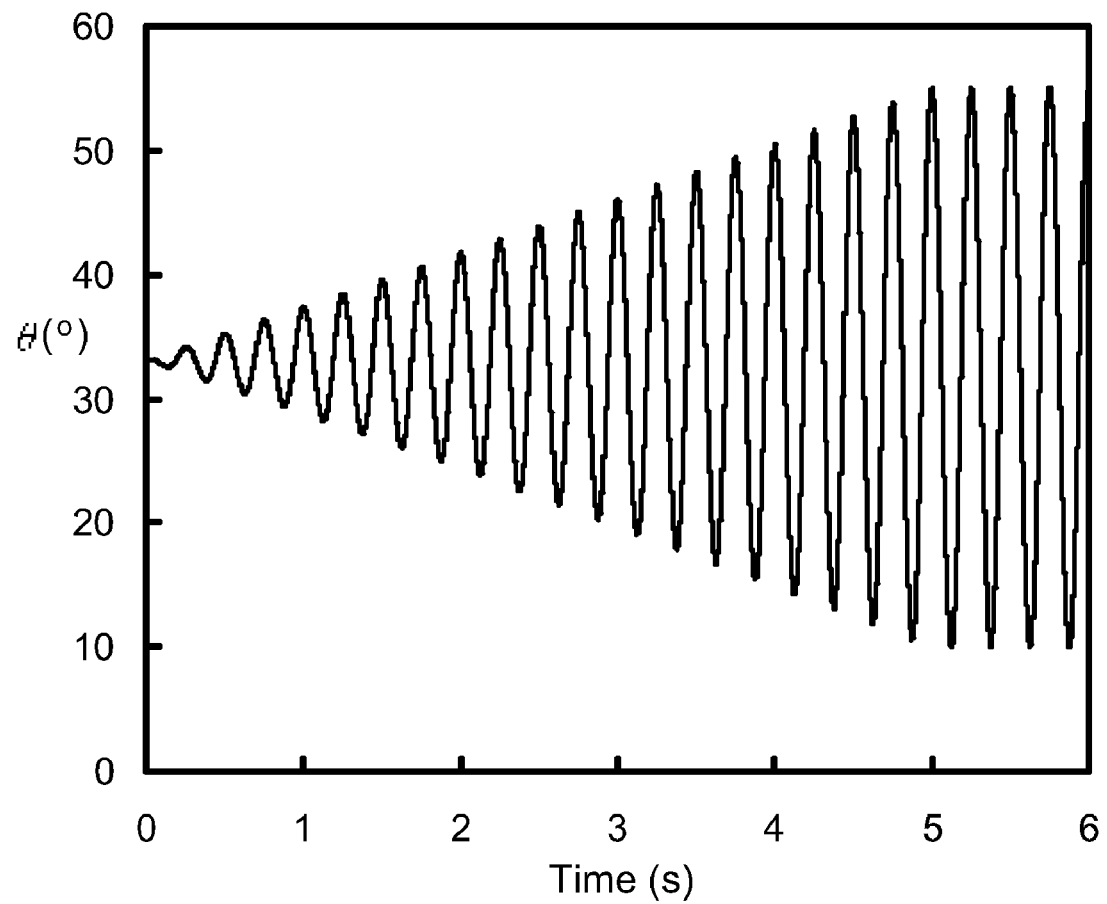
FIG. 6 is a plot illustrating a behavior of a second simulation axis during the startup procedure shown in FIG. 4.

FIG. 6 is a plot of the bend angle as a function of time using the startup procedure shown in FIG. 4. For the purposes of clarity, the desired bend angle profile is not shown in FIG. 6 to more clearly show the bend angle derived from the positions of the scissors and extensor actuators. Although not displayed in FIG. 6, the user-defined bend profile is roughly sinusoidal with a 4 Hz frequency and a peak-to-peak range of about 10° to about 55°. As FIG. 6 indicates, the bend angle starts at roughly the midpoint in the peak-to-peak range and follows a roughly sinusoidal profile at about 4 Hz with gradually increasing amplitude until it matches the user-defined profile at around 5 seconds.

Figure 7:
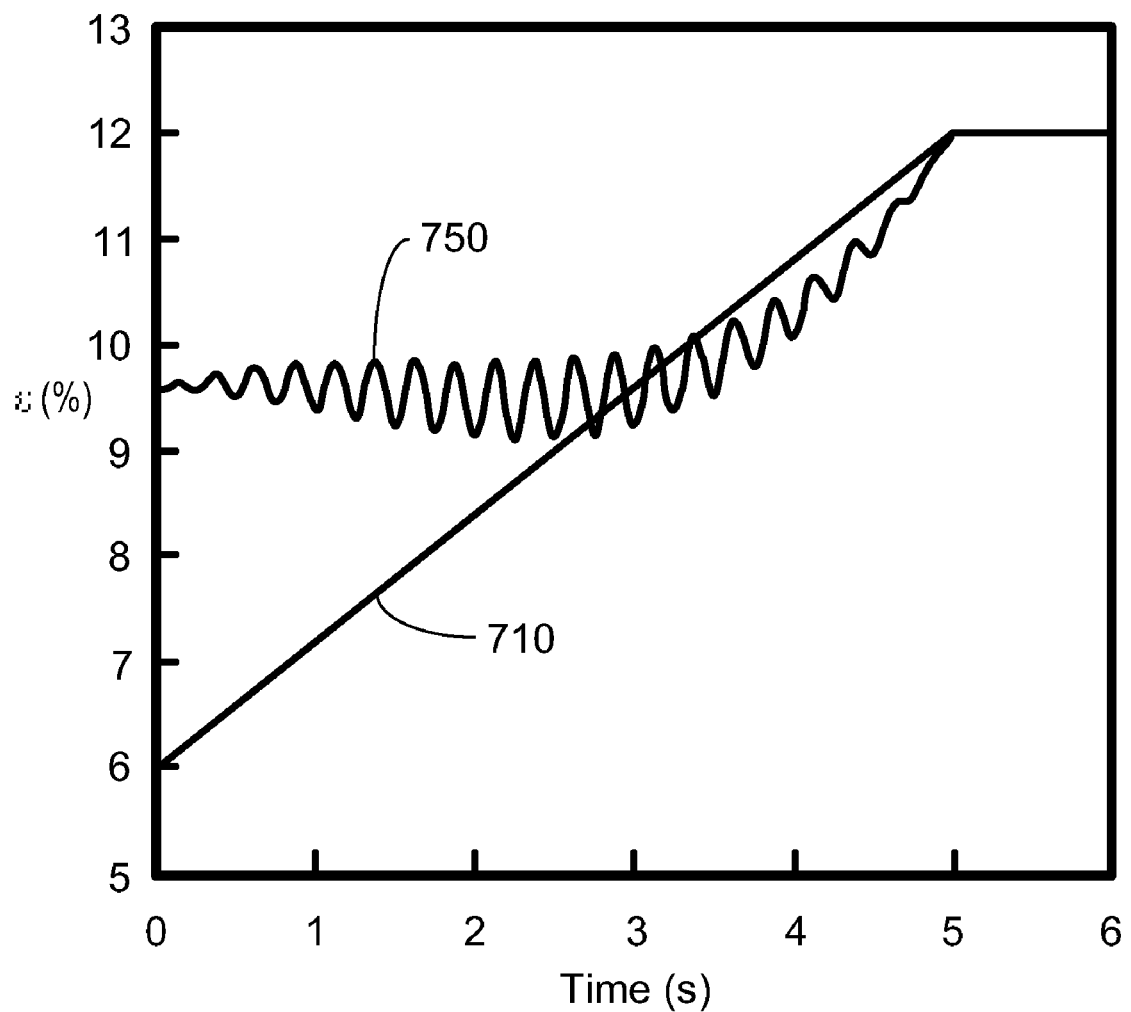
FIG. 7 is a plot illustrating another behavior of a first simulation axis during the startup procedure shown in FIG. 4.

FIG. 7 is a plot of the axial strain as a function of time using the startup procedure shown in FIG. 4. In the example shown in FIG. 7, the user has selected a constant axial strain of about 12% and a bend profile that is roughly sinusoidal with a frequency of about 4 Hz with a peak-to-peak range of 85° to 100°. The desired profile is indicated by reference 710 and includes the user-selected constant axial strain of about 12% after about 5 seconds from startup and a startup ramp starting at roughly one-half of the user-selected axial strain value and increasing to the user-selected value at about 5 seconds. Reference 750 shows the axial strain calculated from the positions of the scissors and extensor actuators. The oscillation in the calculated axial strain is believed to arise because the two actuators are not in the correct position to achieve constant strain and as the amplitude is increased, one of the actuators may reach its desired position before the other actuator reaches its corresponding desired position. As the two actuators reach their respective positions, the amplitude of the axial strain oscillation decreases until it matches the user-selected constant strain of 12%.

Figure 8:
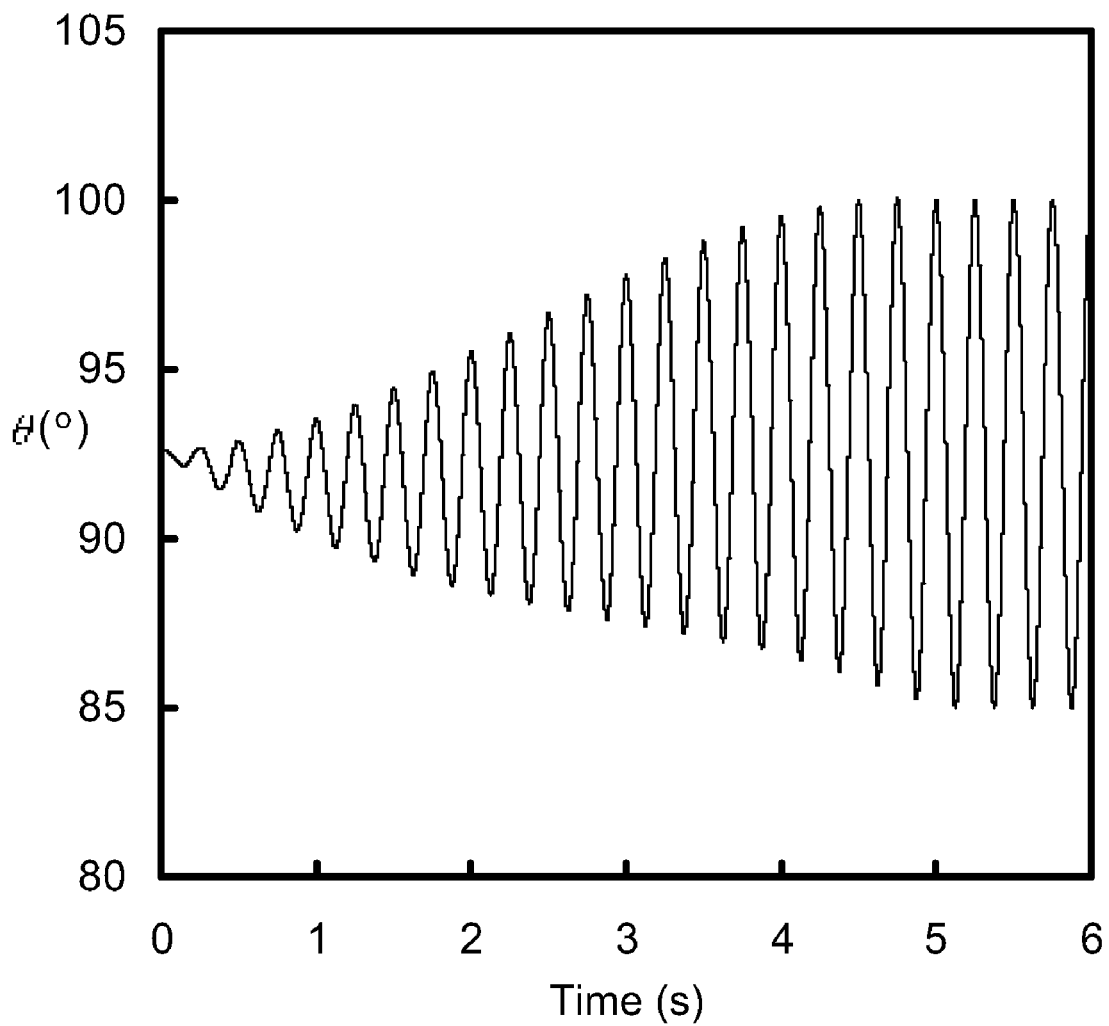
FIG. 8 is a plot illustrating another behavior of a second simulation axis during the startup procedure shown in FIG. 4.

FIG. 8 is a plot of the bend angle as a function of time using the same initial conditions and startup procedure shown in FIG. 7. For the purposes of clarity, the desired bend angle profile is not shown in FIG. 8 to more clearly show the bend angle derived from the positions of the scissors and extensor actuators. The slight asymmetry in the bend angle envelop is believed due to the asymmetric axial strain profile shown in FIG. 7 and the coupling between scissors and extensor actuators.

Embodiments of the systems and methods described above comprise computer components and computer-implemented steps that will be apparent to those skilled in the art. For example, it should be understood by one of skill in the art that the computer-implemented steps may be stored as computer-executable instructions on a computer-readable medium such as, for example, floppy disks, hard disks, optical disks, Flash ROMs, nonvolatile ROM, and RAM. Furthermore, it should be understood by one of skill in the art that the computer-executable instructions may be executed on a variety of processors such as, for example, microprocessors, digital signal processors, gate arrays, etc. For ease of exposition, not every step or element of the systems and methods described above is described herein as part of a computer system, but those skilled in the art will recognize that each step or element may have a corresponding computer system or software component. Such computer system and/or software components are therefore enabled by describing their corresponding steps or elements (that is, their functionality), and are within the scope of the present invention.

Having thus described at least illustrative embodiments of the invention, various modifications and improvements will readily occur to those skilled in the art and are intended to be within the scope of the invention. Accordingly, the foregoing description is by way of example only and is not intended as limiting. The invention is limited only as defined in the following claims and the equivalents thereto.

What is claimed:

1. A startup method for a multi-axis simulation system including a test fixture having a multiple-input-multiple-output linkage, the multiple-input-multiple-output linkage driven by a first actuator and a second actuator, the multiple-input-multiple-output linkage acting on a sample holder to control the position of the sample holder along a first simulation axis and a second simulation axis, the method comprising:
receiving a first simulation axis profile characterized by a first profile amplitude and a second simulation axis profile characterized by a second profile amplitude;
calculating an initial position for the first actuator based on the first simulation axis profile, the second simulation axis profile, and characteristics of the multiple-input-multiple-output linkage;
moving the first actuator to the initial position, the initial position of the first actuator causing the multiple-input-multiple-output linkage to position the sample along the first simulation axis within a subset of a peak-to-peak range of the first simulation axis profile and along the second simulation axis within a subset of a peak-to-peak range of the second simulation axis profile;
operating the first actuator to cause the multiple-input-multiple-output linkage to track the first and second simulation axis profiles and constrain first simulation axis values applied to the sample holder to within the peak-to-peak range of the first simulation axis profile while increasing the first actuator's amplitude from an initial value of zero to the first profile amplitude at a predetermined rate which is less than 10% per cycle.

2. The method of claim 1 wherein the predetermined rate is less than 9% per cycle.

3. The method of claim 1 wherein the predetermined rate is 1% per cycle.

4. The method of claim 1 wherein the first simulation axis is an axial strain.

5. The method of claim 4 wherein the second simulation axis is a bend angle.

6. The method of claim 1 wherein the subset of the range of the first simulation profile comprises a point in a region containing a middle half of a peak-to-peak range of the first simulation profile and the subset of the range of the second simulation profile comprises a point in a region containing a middle half of a peak-to-peak range of the second simulation profile.

7. The method of claim 1 wherein the subset of the range of the first simulation profile comprises a mean value of the first simulation axis profile and the subset of the range of the second simulation profile comprises a mean value of the second simulation axis profile.

8. The method of claim 1 wherein subset of the range of the first simulation profile comprises one-half of a value of the first simulation profile.

9. The method of claim 1 wherein the step of moving includes:
operating the first actuator to disengage a bend tool contacting the sample;
operating the second actuator to an initial position calculated for the second actuator; and
operating the first actuator to the initial position calculated for the first actuator.

10. A non-transitory computer medium containing computer instructions stored therein for causing a computer processor to perform the method of claim 1.

11. A multi-axis simulation system comprising:
a test fixture having a multiple-input-multiple-output linkage, the multiple-input-multiple-output linkage driven by a first actuator and a second actuator, the multiple-input-multiple-output linkage acting on a sample holder to control the position of the sample holder along a first simulation axis and a second simulation axis;
a controller configured to
receive a user-specified first simulation axis profile characterized by a first profile amplitude and a second simulation axis profile characterized by a second profile amplitude,
calculate an initial position for the first actuator based on the first simulation axis profile, the second simulation axis profile, and characteristics of the multiple-input-multiple-output linkage;
move the first actuator to the initial position, the initial position of the first actuator causing the multiple-input-multiple-output linkage to position the sample along the first simulation axis within a subset of a peak-to-peak range of the first simulation axis profile and along the second simulation axis within a subset of a peak-to-peak range of the second simulation axis profile;

operate the first actuator to cause the multiple-input-multiple-output linkage to track the first and second simulation axis profiles and constrain first simulation axis values applied to the sample holder to within the peak-to-peak range of the first simulation axis profile while increasing the first actuator's amplitude from an initial value of zero to the first profile amplitude at a predetermined rate which is less than 10% per cycle.

12. The system of claim 11 wherein the first simulation axis is an axial strain and the second simulation axis is a bend angle.

13. A non-transitory computer medium containing computer instructions stored therein for causing a computer processor to execute a startup procedure on a multi-axis simulation system including a test fixture having a multiple-input-multiple-output linkage, the multiple-input-multiple-output linkage driven by a first actuator and a second actuator, the multiple-input-multiple-output linkage acting on a sample holder to control the position of the sample holder along a first simulation axis and a second simulation axis by:

receiving a first simulation axis profile characterized by a first profile amplitude and a second simulation axis profile characterized by a second profile amplitude;

calculating an initial position for the first actuator based on the first simulation axis profile, the second simulation axis profile, and characteristics of the multiple-input-multiple-output linkage;

moving the first actuator to the initial position, the initial position of the first actuator causing the multiple-input-multiple-output linkage to position the sample along the first simulation axis within a subset of a peak-to-peak range of the first simulation axis profile and along the second simulation axis within a subset of a peak-to-peak range of the second simulation axis profile;

operating the first actuator to cause the multiple-input-multiple-output linkage to track the first and second simulation axis profiles and constrain first simulation axis values applied to the sample holder to within the peak-to-peak range of the first simulation axis profile while increasing an amplitude having an initial value of zero to a value characterizing an amplitude of the first simulation profile at a predetermined rate which is less than 10% per cycle.

14. The non-transitory computer medium of claim 13 further containing computer instructions stored therein for causing the computer processor to:

operate the first actuator to disengage a bend tool contacting the sample;

operate the second actuator to an initial position calculated for the second actuator; and operate the first actuator to the initial position calculated for the first actuator.

* * * * *